(12) United States Patent
Lynch

(10) Patent No.: US 11,523,989 B2
(45) Date of Patent: Dec. 13, 2022

(54) METHOD TO IMPROVE THE HEALTH OF THE MICROBIOME IN A HUMAN GASTROINTESTINAL SYSTEM AND MULTI-CHAMBER PROBIOTIC DELIVERY PRODUCTS THEREFOR

(71) Applicant: ProbioTech LLC, Princeton, NJ (US)

(72) Inventor: Deborah L. Lynch, Princeton, NJ (US)

(*) Notice: Subject to any disclaimer, the term of this patent is extended or adjusted under 35 U.S.C. 154(b) by 0 days.

(21) Appl. No.: 16/229,258

(22) Filed: Dec. 21, 2018

(65) Prior Publication Data
US 2019/0388345 A1 Dec. 26, 2019

Related U.S. Application Data

(62) Division of application No. 16/016,175, filed on Jun. 22, 2018.

(51) Int. Cl.
| | | |
|---|---|---|
| A61K 9/02 | (2006.01) | |
| A61K 35/745 | (2015.01) | |
| A61K 9/00 | (2006.01) | |
| A61K 35/742 | (2015.01) | |
| A61K 35/747 | (2015.01) | |
| A61K 9/48 | (2006.01) | |
| A61K 35/00 | (2006.01) | |
| A61K 36/28 | (2006.01) | |
| A61K 36/889 | (2006.01) | |
| A61K 36/73 | (2006.01) | |

(52) U.S. Cl.
CPC ............ *A61K 9/025* (2013.01); *A61K 9/0031* (2013.01); *A61K 9/0036* (2013.01); *A61K 9/0053* (2013.01); *A61K 9/4808* (2013.01); *A61K 9/4816* (2013.01); *A61K 35/742* (2013.01); *A61K 35/745* (2013.01); *A61K 35/747* (2013.01); *A61K 36/28* (2013.01); *A61K 36/73* (2013.01); *A61K 36/889* (2013.01); *A61K 2035/115* (2013.01)

(58) Field of Classification Search
CPC ...... A61K 9/025; A61K 35/745; A61K 36/28; A61K 36/889; A61K 36/73; A61K 9/0053; A61K 35/742; A61K 35/747; A61K 9/4816; A61K 9/4808; A61K 9/0031; A61K 9/0036; A61K 2035/115; A61K 2035/126; A61K 9/0034; A61K 36/82

See application file for complete search history.

(56) References Cited

U.S. PATENT DOCUMENTS

| | | |
|---|---|---|
| 4,347,237 A | 8/1982 | Evenstad et al. |
| 8,361,497 B2 | 1/2013 | Miller |
| 8,802,161 B2 | 8/2014 | Mazzio et al. |
| 8,853,269 B2 | 10/2014 | Mosbaugh et al. |
| 2005/0191346 A1 | 9/2005 | Nowal et al. |
| 2006/0115465 A1 | 6/2006 | Macfarlane et al. |
| 2008/0274162 A1 | 11/2008 | Nessa et al. |
| 2010/0143533 A1 | 6/2010 | Chang et al. |
| 2011/0070334 A1 | 3/2011 | Rangavajla |
| 2012/0245123 A1* | 9/2012 | Lopez Pedrosa .... A61K 31/733 514/60 |
| 2013/0108599 A1 | 5/2013 | Comeaux |
| 2013/0209612 A1 | 8/2013 | Michalowski et al. |
| 2016/0199424 A1* | 7/2016 | Berry ................. A61K 9/0031 424/93.3 |
| 2017/0173091 A1 | 6/2017 | Lynch |
| 2018/0078585 A1* | 3/2018 | Mulder ................. A61K 39/09 |

FOREIGN PATENT DOCUMENTS

| | | |
|---|---|---|
| CN | 102475887 A | 5/2012 |
| EP | 1514553 B1 | 2/2008 |
| EP | 3187175 A1 | 7/2017 |
| FR | 3008317 A1 | 1/2015 |
| WO | 2017083549 A1 | 5/2017 |
| WO | 2017137496 A1 | 8/2017 |

OTHER PUBLICATIONS

AAPS PharmSciTech, vol. 19, No. 8, Nov. 2018, Vivian Gray, pp. 3328-3332. (Year: 2018).*
PLoS One. 2014; 9(5): e98031. (Year: 2014).*
Anonymous, "Prebiotics/Probitics"; The University of North Dakota Dining Services (2010) downloaded from: https://www.und.edu/student.-life/dining/_files/docs/fact-sheets/probiotics.pdf on Jun. 30, 2017.
Anonymous, "Typical Fatty-Acid Compositions of Some Common Fats"; downloaded from: http://www.web.pdx.edu/~wamserc/C336S12/fat.pdf on Jun. 30, 2017.
Hidaka et al. Effects of Fructooligosaccharides on Intestinal Flora and Human Health; Bifidobacteria Microflora, vol. 5, No. 1 pp. 37-50, 1986.
International Search Report for International Application No. PCT/US2019/037260, dated Oct. 9, 2019, 3 pages.
Written Opinion for International Search Report for PCT/US2019/037260, dated Oct. 9, 2019, 7 pages.
International Search Report for International Application No. PCT/US2019/037260, dated Aug. 27, 2019, 2 pages.
Written Opinion for International Search Report for International Application No. PCT/US2019/037260, dated Aug. 27, 2019, 7 pages.
Extended EP Search Report, EP Application No. 19821547.7, dated Mar. 4, 2022.

* cited by examiner

*Primary Examiner* — Hasan S Ahmed
(74) *Attorney, Agent, or Firm* — Saul Ewing Arnstein & Lehr LLP; Justin Crotty

(57) ABSTRACT

A method for treating the gastro-intestinal or a urogenital system of a subject with prebiotic nutrients and probiotic bacteria is provided. Multi-chamber products are described which include at least two chambers wherein probiotic bacteria or human microbiome transplants are contained in one or more inner chambers and wherein prebiotic nutrients are contained in an outer chamber, the outer chamber completely enclosing the inner chamber(s). One or both chambers may contain a pharmaceutically acceptable material that is solid outside the human body when in a dry environment, but that melts at internal body temperature. The products may be administered by oral, rectal, vaginal, or urethral routes.

8 Claims, 8 Drawing Sheets

METHOD TO IMPROVE THE HEALTH OF THE MICROBIOME IN A HUMAN GASTROINTESTINAL SYSTEM AND MULTI-CHAMBER PROBIOTIC DELIVERY PRODUCTS THEREFOR

CROSS-REFERENCE TO RELATED APPLICATIONS

This application is a Rule 53(b) divisional of U.S. patent application Ser. No. 16/016,175, filed Jun. 22, 2018. The entire disclosure of the aforementioned patent application is hereby incorporated herein by reference.

BACKGROUND OF THE INVENTION

The human gastrointestinal tract has trillions of microbes that are living in the intestinal track from the mouth to the rectum. These microbes appear to play a major role in the health and wellness of each individual and the absence of certain microbes is believed to be a cause of disease in individuals. Research in human and animal models has shown that those who have an elevated body mass index (BMI) in the obese range and/or who suffer from type 2 diabetes appear to have a different bacterial milieu than those without these conditions. In fact, when the microbiota from obese humans or animals are transferred to healthy animals of average weight, but devoid of bacteria of their own, these recipient animals appear to have a greater risk of eventually becoming obese or diabetic. In addition, rheumatoid arthritis, muscular dystrophy, multiple sclerosis, depression, fibromyalgia, and possibly some cancers have been linked to an altered or unfavorable microbiome. Studies have suggested that probiotics may impact the function of colonizing microbes.

The human gut is a complex ecosystem where microbiota, nutrients, and host cells interact extensively, a process crucial for functional homeostasis. Any imbalance could have negative health consequences and many diseases have been associated with impairment of the gut microbiota. Probiotics are "live micro-organisms that when administered in adequate amounts confer a health benefit on the host" (World Health Organization, 2001). Studies suggest that supplementing bacteria via probiotics may promote homeostasis of the gut microbiota rather than change its composition. Prebiotic nutrients selectively target and stimulate the growth and activity of beneficial bacterial species in the gut microbiota that confer health benefits to the host. These close relationships between gut microbiota, health, and disease, have led to great interest in using probiotics or prebiotic nutrients (i.e. non-digestible substrates) to positively modulate and normalize the gut microbiota to prevent or treat some diseases.

The different compartments of the gastrointestinal system or urogenital system (or tract) are inhabited by populations of micro-organisms which constitute each person's unique personal microbiome. One of the most important microbiomes is in the colon. In the colon, 'normobiosis' characterizes a composition of the gut ecosystem in which micro-organisms with potential health benefits predominate over potentially harmful ones, in contrast to 'dysbiosis', in which potentially harmful micro-organisms are dominant, thus creating a disease-prone situation, such as acute and chronic diarrhea, or chronic debilitating diseases like Inflammatory Bowel Disorder and Irritable Bowel Syndrome.

The mucosal epithelia of the gut provide an enormous surface area for invading pathogens to gain access to the internal environment of the body. The very characteristics that make the mucosa excellent at physiological support of metabolism, such as nutrient absorption, also confer vulnerability to pathogenic invasion and infection. The integrity of this barrier can be enhanced by probiotics in a number of ways. Lactobacilli and bifidobacteria compete for adhesive access to attachment sites on epithelial cells, and displace pathogenic bacteria which might dominate in the host microbiome. Combinations of multiple probiotic strains can increase beneficial health effects as compared with individual strains by exerting synergistic mucosal adhesion effects and decreasing the proportion of pathogenic bacteria.

Data suggest that the bacteria in the lower gastrointestinal system have a direct interaction with human health. There are two kinds of nourishment: nourishment of the human body and the nourishment of the existing microbiome cells. Because of this, there appears to be a direct link to the bacteria in the rectal mucosa of humans and their ability to prevent disease or be more susceptible to disease. Therefore, by providing the rectum with healthy bacteria or providing nourishment to the existing bacteria present in the human gut, the consumer will populate the intestinal mucosa with desirable bacteria and nourish them. In this way, the suppository of the present invention can promote and support overall human health.

The intestines are a long, continuous tube running from the stomach to the anus. The absorption of nutrients and water occurs primarily in the intestines. The intestines include the small intestine, large intestine, and rectum. The large intestine performs the vital functions of converting food into feces, absorbing essential vitamins produced by gut bacteria, also referred to as the microbiome. Bacterial fermentation converts the chyme into feces and releases vitamins, including vitamins K, B1, B2, B6, B12, and biotin. Vitamin K is almost exclusively produced by the gut bacteria and is essential in the proper clotting of blood. Gases such as carbon dioxide and methane are also produced as a byproduct of bacterial fermentation and lead to flatulence. The entire digestive system, including the mouth, esophagus, stomach, small intestine and colon, make up one long tube that must act like the skin to protect the blood and inner organs against harmful materials. In fact, the lining of the digestive system is continuous with the skin at the mouth and anus, making the skin and the lining of the digestive passageway one continuous barrier that protects the blood and inner organs against harmful substances in the environment. There are data that suggest the microbiome in the rectal area of the gastrointestinal tract assists in maintaining a healthy immune system in both males and females, which the present invention accomplishes by inserting healthy or desirable bacteria directly into the rectum.

A major issue in healthcare today is how to populate humans with a microbiome that may be able to support or restore health. To date, the three major ways of delivering healthy or desirable bacteria to the human in an attempt to promote health are:

1. Through food and drinks. Many products such as prebiotic nutrients and probiotics are currently marketed with this claim. Probiotics are found in foods such as certain yogurts and kefirs, while prebiotic nutrients are found in whole grains, bananas, onions, garlic, honey and artichokes. In addition, probiotics and prebiotic nutrients are added to some foods and are available as dietary supplements. In addition, everyday foods such as miso, sauerkraut, pickles, kimchi, kombucha tea and other fermented foods are believed contribute to promote a healthy intestinal microbiome.

2. Through oral ingestion of capsules and tablets containing probiotics. Since the gastric acids in our stomachs destroys so much of the probiotic bacteria, commercial brands develop products containing a range of from million to billions of probiotic bacteria. The actual amounts delivered to the lower intestinal tract where they are needed are unknown.

3. Through fecal microbiota transplant (FMT), the process of transplantation of fecal bacteria matched from a healthy individual into an unhealthy recipient. FMT involves restoration of the colonic microflora by introducing healthy bacterial flora through infusion of donor stool, e.g. by enema, orogastric tube, by mouth, or by other implantation means, in the form of a capsule containing freeze-dried material, obtained from a healthy donor. Previous terms for the procedure include fecal bacteriotherapy, fecal transfusion, fecal transplant, stool transplant, fecal enema, and human probiotic infusion (HPI).

Each of the foregoing methods lacks the ability to directly deliver healthy probiotic bacteria to the rectal area or the vaginal area. Conventionally, probiotic products are formulated with live probiotic bacteria embedded in a solid or semisolid matrix or with freeze-dried bacteria enclosed in a capsule or pouch. There is no consideration of the fact that these live bacteria only exert biological efficacy after interacting with a potentially unresponsive host microbiome, which may or may not be receptive to externally administered probiotic bacteria.

SUMMARY OF THE INVENTION

In one aspect, the invention provides a method for delivering probiotic bacteria to the gastrointestinal system or urogenital system of a subject in need thereof comprising the steps of:
first administering to the gastrointestinal system or urogenital system of the subject a prebiotic nutrient in an amount effective to improve the receptivity of the gastrointestinal system or urogenital system to probiotic bacteria, and
second, administering probiotic bacteria to the gastrointestinal system or urogenital system of the subject.

In various embodiments, the prebiotic nutrient is selected from the group consisting of plant-derived oils, animal-derived oils and fatty acids, fruit vinegars, acetic acid, butyric acid, butyrate, complex carbohydrates, fibers, apple cider vinegar, iron, calcium, potassium, vitamin B12, vitamin C and vitamin K, polyethylene glycol, hydrogels, cocoa butter, glycerinated gelatin, shea butter, petrolatum, mineral oil, shark liver oil, Vitamin A, Vitamin $B_6$, Vitamin D, Vitamin $K_2$ (MK 1), potassium, folic acid, L-carnitine, quercetin, magnesium, calcium, alpha-lipoic acid, fiber, omega-3 fatty acids, nuclear factor-like 2 activators, L-glutathione, L-glutamate and gamma-aminobutyric acid, lemon juice, lactic acid, chamomile, coenzyme Q-10, collagen, gelatin, green tea extract, lactose, galactose, fructose, fructose oligosaccharides, iso-maltose, dextrose, glucose, amylopectin, inulin, resistant starch, corn starch, oligosaccharides, rosemary leaf extract, oregano oil, curcumin, coffee, ginger, flax seed oil, green barley, agrimony, aniseed-basil, aniseed-fennel, cayenne, Echinacea, garlic, honey, molasses, horseradish, lavender, marshmallow, olive oil, milk, peppermint, slippery elm, buttermilk, goldenrod, St John's wort, uva ursi, yarrow, bee pollen, bee propolis, mint and mixtures thereof.

In various embodiments, the prebiotic nutrient is apple cider vinegar.

In various embodiments, the prebiotic nutrient is blended into a mixture of fatty acids containing at least 90 wt. % saturated fatty acids.

In various embodiments, at least 50 wt. % of the saturated fatty acids of the mixture of fatty acids is lauric acid.

In various embodiments, the mixture of fatty acids includes coconut oil.

In various embodiments, the probiotic bacteria comprise one or more purified bacterial species and strains selected from the group consisting of *Lactobacillus rhamnosus, Bifidobacterium lactis, Lactobacillus plantarum, Lactobacillus acidophilus, Lactobacillus brevis, Lactobacillus gasseri, Bifidobacterium longum, Lactobacillus salivarius, Lactobacillus casei, Lactobacillus jensenii, Lactobacillus lactis, Bifidobacterium bifidum, Streptococcus thermophilus*, and mixtures thereof.

In various embodiments, the probiotic bacteria include human microbiome transplant samples collected from the human colon, rectum, vagina, urethra, skin, mouth, or throat.

In another aspect, the invention provides a method for directly delivering healthy probiotic bacteria to the urogenital system of a subject in need thereof comprising the sequential steps of:
administering to the urogenital system of the subject a prebiotic nutrient compound in an amount effective to improve the receptivity of the urogenital system for the probiotic,
administering selected probiotic bacteria to the urogenital system containing the prebiotic nutrient compound.

In another aspect, the invention provides a multi-chamber dosage form comprising:
a) an inner chamber containing one or more species of probiotic;
b) a pharmaceutically acceptable matrix material that is solid at room temperature when in a dry environment, but that melts at body temperature when in contact with the mucosa of the rectum or vagina of the subject, wherein the matrix material fully encloses the inner chamber;
wherein the matrix material contains prebiotic nutrients for said probiotic bacteria and a mixture of fatty acids that are solid at room temperature but melt at a subject's body temperature, and
wherein the dosage form is a capsule, a capsule embedded in suppository, a capsule embedded in prefilled applicator or a capsule embedded in prefilled sealed pouch.

In various embodiments, wherein said source of prebiotic nutrients comprises apple cider vinegar.

In various embodiments, wherein said mixture of fatty acids comprises at least 90 wt. % of saturated fatty acids.

In various embodiments, at least 50 wt. % of the saturated fatty acids of said mixture of fatty acids is lauric acid.

In various embodiments, said mixture of fatty acids comprises coconut oil.

In various embodiments, said probiotic bacteria comprise one or more species of bacteria selected from the group consisting of *Lactobacillus rhamnosus, Bifidobacterium lactis, Lactobacillus planetarium, Lactobacillus acidophilus, Lactobacillus casei, Lactobacillus brevis, Bifidobacterium longum, Lactobacillus salivarius, Lactococcus lactis, Lactobacillus reuterii, Lactobacillus crispatus, Lactobacillus inners, Lactobacillus jensenii, Bacillus coagulans, Lactobacillus bulgaricus, Lactobacillus gasseri, Bifidobacterium bifidum* and mixtures thereof.

In another aspect, the invention provides a dosage form for the delivery of probiotic bacteria and prebiotic nutrients to the gastrointestinal tract of a subject to supplement and nourish the existing microbiome thereof, the dosage form comprising two chambers, characterized by an inner first chamber containing one or more species of probiotic bacteria and an outer second chamber containing a source of nutrition for the probiotic bacteria and for the existing microbiome, wherein the source of nutrition is blended into a fatty acid matrix comprising a mixture of fatty acids that are solid at room temperature when in a dry environment, but that melts at body temperature when in contact with the mucosa of the gastrointestinal tract of the subject.

In various embodiments, the dosage form is a capsule.

In various embodiments, the dosage form is a capsule suitable for oral ingestion.

In various embodiments, the dosage form is a suppository.

In various embodiments, said mixture of fatty acids comprises at least 90 wt. % of saturated fatty acids and the source of nutrients comprises apple cider vinegar.

In various embodiments, said mixture of fatty acids comprises coconut oil.

In another aspect, the invention provides a multi-chamber dosage form comprising:

(a) an inner first chamber containing one or more species of probiotic bacteria, and (b) an outer second chamber containing a prebiotic nutrient for the probiotic bacteria and for the existing microbiome, the first chamber and the second chamber being separated by at least one wall, wherein the inner chamber is completely enclosed by the outer chamber, and wherein the multi-chamber dosage form is adapted to be inserted into a rectum or vagina of a subject and wherein the outer chamber is solid at room temperature when in a dry environment, but melts at body temperature when in contact with the mucosa of the subject's rectum or vagina and wherein the multi-chamber dosage form is a capsule, a suppository, a capsule embedded within a prefilled applicator or a capsule embedded within a sealed pouch.

A method for improved delivery of probiotic bacteria to the gastrointestinal system or urogenital system of a subject in need thereof comprising administering to the subject a multi-chamber dosage form, wherein following administration, the dosage form first releases a prebiotic to the gastrointestinal system or urogenital system of the subject in an amount effective to improve the receptivity of the gastrointestinal system or urogenital system to one or more species of probiotic bacteria and then releases one or more species of probiotic bacteria to the gastrointestinal system or urogenital system of the subject, thereby improving delivery of probiotic bacteria to the gastrointestinal system or urogenital system of a subject.

In various embodiments, the multi-chamber dosage form comprises:

a) an inner chamber containing one or more species of probiotic;

b) a pharmaceutically acceptable matrix material that is solid at room temperature when in a dry environment, but that melts at body temperature when in contact with the mucosa of the rectum or vagina of the subject, wherein the matrix material fully encloses the inner chamber;

wherein the matrix material contains prebiotic nutrients for said probiotic bacteria and a mixture of fatty acids that are solid at room temperature but melt at a subject's body temperature.

In various embodiments, the dosage form is a capsule, a capsule embedded in suppository, a capsule embedded in prefilled applicator or a capsule embedded in prefilled sealed pouch.

The various embodiments herein may apply to each of the aspects of the invention. The embodiments are not intended to be interpreted as applying only to the aspect with reference to which they are specifically described.

BRIEF DESCRIPTION OF THE DRAWINGS

The following detailed description of various embodiments of the invention will be better understood when read in conjunction with the appended drawings. For the purpose of illustrating the invention, there are shown in the drawings certain specific embodiments. It should be understood, however, that the invention is not limited to the precise arrangements and instrumentalities of the embodiments shown in the drawings.

DETAILED DESCRIPTION OF THE INVENTION

Figure 1:
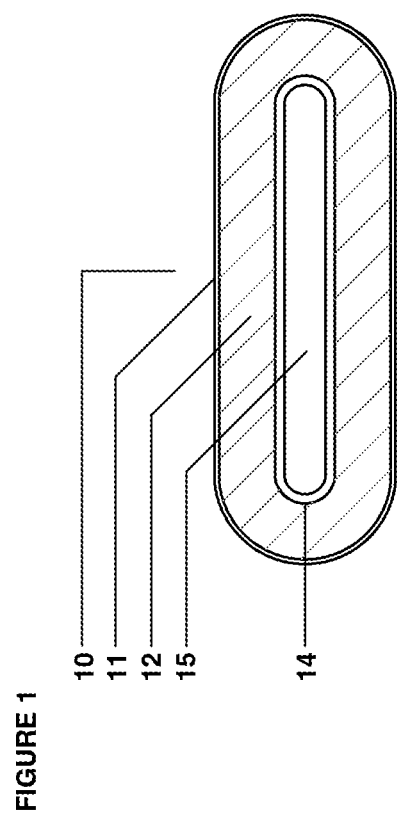
FIG. 1 is a cross-sectional side view of a multi-chamber dosage form in accordance with the present invention.

In accordance with the present invention, there is provided a method for treating the gastrointestinal system or urogenital system of a human subject to directly deliver healthy probiotic bacteria to the subject's gastrointestinal system or urogenital system, respectively. The method comprises administering to the subject's gastrointestinal system or urogenital system a prebiotic nutrient compound in an amount effective to improve the receptivity of the gastrointestinal system or urogenital system to a probiotic bacteria and then administering the probiotic bacteria to the gastrointestinal system or urogenital system containing the prebiotic nutritional compound.

As used herein, "subject" refers to any animal, or cells thereof whether in vitro or in situ, amenable to the methods described herein. In certain non-limiting embodiments, the subject is a mammal. In certain non-limiting embodiments, the subject is a human. In certain non-limiting embodiments, the subject is a human female.

As used herein, in the context of probiotics and the gastrointestinal or urogenital system, the term "receptivity" refers to the state of host tissue which enables and facilitates incorporation or integration of probiotic bacteria. Receptivity is improved when delivery of a probiotic has a greater beneficial impact on the subject's microbiome relative to a microbiome not exposed to the agent or condition responsible for the improvement. In various embodiments, receptivity may be evaluated based on an increased number of bacteria or on the presence of species of beneficial bacteria and absence of harmful bacteria and a bacterial spectrum that more closely resembles a healthy microbiome.

The present invention also provides several novel dosage forms that are capable of delivering the two step prebiotic/probiotic treatment method, described above. One dosage form is a multi-chamber dosage form having at least two chambers; an outer chamber and an inner chamber. The outer chamber completely defines an exterior surface of the multi-chamber dosage form and contains prebiotic nutrients. The outer chamber also contains one or more inner chambers containing probiotic bacteria. The inner chamber(s) are completely surrounded by the outer chamber.

According to another embodiment of the present invention, a dosage form is provided for the delivery of probiotic bacteria and prebiotic nutrients to the gastrointestinal tract to supplement and nourish the existing microbiome of a subject, wherein the dosage form is a two-chamber dosage form with an inner first chamber containing one or more species of probiotic bacteria dispersed within the fatty acid matrix and a second outer chamber containing prebiotic nutrients for the probiotic bacteria and for the existing microbiome.

According to another embodiment of the present invention, a dosage form is provided for the delivery of probiotic bacteria and prebiotic nutrients to the urogenital tract to supplement and nourish the existing microbiome of a subject, wherein the dosage form is a two-chamber dosage form with an inner first chamber containing one or more species of probiotic bacteria dispersed within the fatty acid matrix and a second outer chamber containing prebiotic nutrients for the probiotic bacteria and for the existing microbiome.

In another embodiment, the prebiotic nutrients and probiotic bacteria are individually blended in a suitable matrix, wherein the matrix is composed of one or more pharmaceutically acceptable ingredients which are solid at conventional room temperature (about 70° F.) and which melt when in contact with a subject's internal body temperature. The individually blended components are used to fill the inner and outer chambers of the multi-chamber dosage form such that the matrix containing the prebiotic nutrients is located in the outer chamber where it contacts a subject's gastrointestinal tract followed by the matrix in the inner chamber containing the probiotic bacteria. Examples of pharmaceutically acceptable matrix materials are fatty acids such as coconut oil, shea butter, cocoa butter, glycerin, polyethylene glycol, glycerinated gelatin, petrolatum, mineral oil, shark liver oil, and the like.

In another embodiment, a multi-chamber dosage form has one or more inner probiotic chambers embedded in an outer prebiotic nutrient formulation all of which is encased within an applicator. The prefilled applicator is adapted to be inserted and dispensed in a subject for rectal or vaginal administration of the capsule.

In particular, the invention provides a sequential, two-step method for treating the gastrointestinal system or urogenital system of a human subject to directly deliver healthy probiotic bacteria to the subject's gastrointestinal system or urogenital system. The method comprises, first administering to the gastrointestinal system or urogenital system a prebiotic nutrient compound in an amount effective to improve the receptivity of the gastrointestinal system or urogenital system to a probiotic and then second, administering probiotic bacteria to the gastrointestinal system or urogenital system containing the prebiotic nutrient compound. The method may be effected through the use of the one or more novel dosage forms (disclosed herein) that are specifically adapted to provide the two-step delivery mechanism designed to enhance probiotic efficacy by first improving the condition of the host mucosal microenvironment, followed by release of an effective amount of probiotic bacteria to that environment. Thus the target tissue site in the gastrointestinal or urogenital tract is first modified by contact with prebiotic nutrients in an amount effective to improve host tissue receptivity and provide a source of nutrition for the probiotic bacteria. This is followed quickly by contact with probiotic bacteria in an amount effective to promote a healthy biome in the improved host tissue area. It has been found that individuals in disease states are often particularly adverse to the survival and proliferation of endogenous and exogenous beneficial probiotic bacteria. The current two-step delivery mechanism has been found to encourage proliferation and persistence of the administered exogenous probiotic bacteria.

An advantageous feature of the present invention is that the outer prebiotic nutrients contact the area intended for treatment prior to the release of the probiotic bacteria within the inner chamber to that area. In accordance with the present invention, the probiotic bacteria will be released from the inner chamber at least 30 seconds after the prebiotic nutrients in the outer chamber have contacted the intended treatment area of the subject. In an advantageous embodiment, the probiotic bacteria will be released from the inner chamber between 0.5 to 60 minutes after the prebiotic nutrients in the outer chamber have contacted the treated area of the subject. It is of course possible to include some amount of probiotic bacteria with the prebiotic nutrients in the outer chamber without deviating from principles of the current invention, provided however that an effective amount of probiotic bacteria is delivered to the target tissue site from an inner chamber subsequent to the delivery of the prebiotic nutrients to that site. The delayed release of the probiotic bacteria relative to the prebiotic nutrients can be effected by numerous techniques that are known to those skilled in the art of sustained release dosage forms. Such techniques include slower dissolving capsule wall materials which may be used to form an inner chamber of the dosage form or alternatively the probiotic bacteria may be enteric coated to slow their release in the subject's gastrointestinal or urogenital tract. Other commonly used techniques known to those skilled in the art may also be used, provided of course that they are capable of delivering the probiotic bacteria in accordance with the foregoing relative dissolution rates.

The present invention is useful to nourish and/or supplement the microbiome of the human lower gastrointestinal tract or urogenital tract with desirable probiotic bacteria. Therefore, according to one embodiment of the present invention, a method is provided for improving the microbiome in the gastrointestinal or urogenital tract of a subject by supplementing the existing probiotic bacteria with additional probiotic bacteria or through nourishment provided to the existing gut bacteria in the microbiome of the rectum or vagina by inserting into the rectum or the vagina, respectively, the multi-chamber dosage form of the present invention.

When used to treat the gastrointestinal tract, the compositions of the present invention provide an alternative to fecal microbiota transplantation in which the transplanted probiotics can be selected and quantities titered to address the needs of an individual patient's microbiome. This represents an improvement over existing treatments in which clinicians attempt to match the bacterial profile of donor stool to the microbiome needs of a patient. Therefore, according to another aspect of the present invention, a microbiota transplantation method is provided for a patient in need thereof, in which a composition according to the present invention is formulated to supply the microbiome needs of a particular patient and then administered to the gastrointestinal tract of the patient.

While intended primarily for the introduction of desirable probiotic bacteria into the lower gastro-intestinal tract microbiome of men and woman via the rectum, the present invention, when inserted into the vagina, has been found to be effective for supplementing or nourishing the bacteria of the vagina of a female subject. Therefore, according to another aspect of the present invention, a method is provided for delivering desirable bacteria and/or supplying nourishment into the microbiome of the vagina by a woman inserting into her vagina the multi-chamber dosage form of the present invention.

The present invention may be made in a manner similar to the manufacturing processes used to make rectally and vaginally inserted products. The multi-chamber dosage forms may be used by digital insertion or by inserting an applicator through the anus into the rectum, thereby bypassing the stomach and upper intestines. The multi-chamber dosage forms may alternatively be used by digital insertion or by using an applicator into the rectum or vagina through the introitus therefore bypassing the stomach and upper intestines. The described multi-chamber dosage forms in this invention may be inserted by the subject in the same manner as over the counter rectal suppositories, or vaginal capsules or suppositories are administered. The encapsulated multi-chamber dosage form can also be taken orally provided, of course, that the probiotic bacteria are enteric coated or otherwise protected from gastric juices in a subject's body, to thereby protect the viability of the probiotic bacteria until they reach the intestine of the subject.

The invention is described in more detail with respect to aforementioned drawings that serve to aid in the description of the invention but do not limit the invention.

FIG. 1 depicts a multi-chamber dosage form 10 in accordance with the present invention. The multi-chamber dosage form 10 contains a matrix material 12 containing prebiotic nutrients in an outer chamber defined by outer chamber wall 11. The multi-dosage form 10 further contains probiotic bacteria in an inner chamber defined by an inner chamber wall 14. The probiotic bacteria within the inner chamber may also optionally be dispersed within a matrix material comprising one or more fatty acids. The inner chamber wall 14 separates the inner chamber from the outer chamber 11 and can function to slow the release of the probiotic bacteria until the matrix material has contacted the target tissue site in a subject's gastrointestinal or urogenital tract, allowing the prebiotic nutrients to improve host tissue receptivity.

Figure 2:
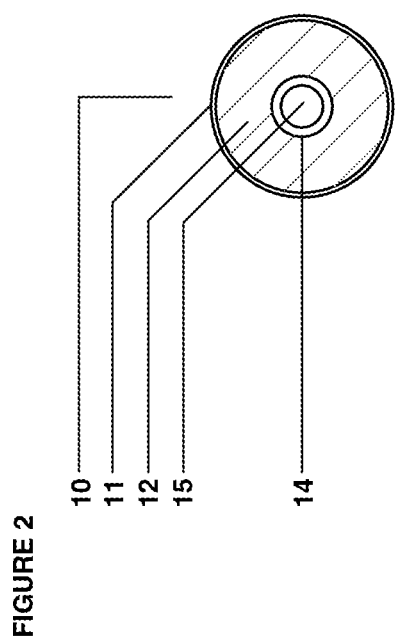
FIG. 2 is a cross-sectional end view of the dosage form shown in FIG. 1.

FIG. 2 illustrates a cross-sectional view of the multi-chamber dosage shown in FIG. 1. While the cross-section view shows a generally circular form, corresponding to a cylindrical dosage form, the shape is not critical to the invention, and other commonly used capsule or suppository shapes are acceptable such as ovoid, hexagonal, octagonal, and the like. As shown in FIGS. 1 and 2, the inner chamber as defined by the inner chamber wall 14 is completely enclosed within the outer chamber 11.

Figure 3:
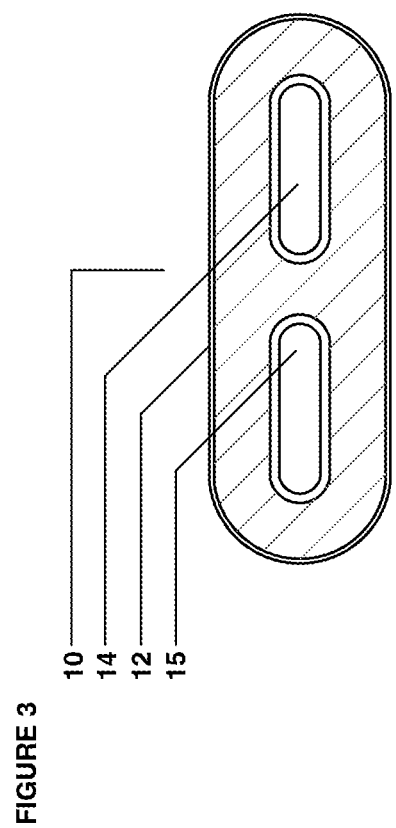
FIG. 3 depicts a cross-sectional side view of an alternative embodiment of the multi-chamber dosage form of the present invention having two inner chambers surrounded by an outer chamber.

FIG. 3 depicts the multi-chamber dosage form 10 of the invention wherein there are two inner chambers defined by inner chamber walls 14 and 17, respectively, each being surrounded by matrix material 12 in an outer chamber defined by outer chamber wall 11. In accordance with this embodiment of the present invention the additional inner chamber 17 may optionally contain additional benefit agents such as an anti-inflammatory agents, vitamins, and the like and combinations thereof.

Figure 6:
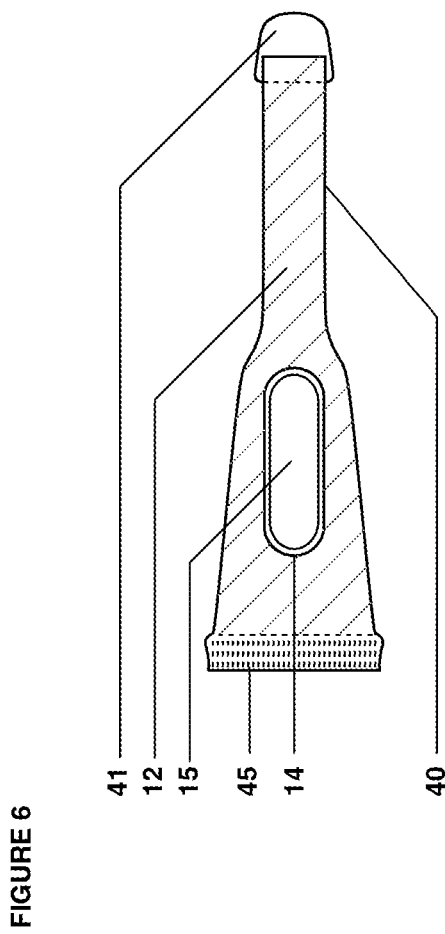
FIG. 6 depicts a cross-sectional view of an alternative applicator containing the-multi-chamber dosage form of the present invention.

The multi-chamber dosage form may be a capsule form as shown in FIG. 1 or in the form of a suppository as shown in FIG. 6. When in capsule form, it may be hard or soft. They may optionally be coated with an enteric coating formulated to dissolve at a predetermined gastrointestinal location. The capsules may be formed using conventional materials such as gelatin, vegetable or synthetic materials. When in suppository form, the outer chamber may be formed by conventional suppository methods and materials, provided of course that the outer chamber contains prebiotic nutrients. The multi-chamber dosage forms for rectal or vaginal delivery may also be formulated as gel capsules, hydrogels, hydrogel capsules, or freeze dried for delivery by tubing, or for delivery by a rectal or vaginal applicator. Referring again to FIG. 1, the outer wall forming the outer chamber 11 may be formed from a gelatin coating or from an enteric coating formulated to dissolve at a predetermined gastrointestinal location.

One method according to the present invention supplements and nourishes the microbiome of the lower gastrointestinal tract of a person by orally ingesting the multi-chamber dosage form of the present invention. In accordance with this embodiment, the multi-chamber dosage form is advantageously enteric coated to protect the probiotic bacteria from the strong acids of the upper digestive tract. The product may be administered orally with a frequency and quantity typical for a probiotic treatment regimen, i.e. as done with conventional probiotic products taken orally on a daily basis the current multi-chamber probiotic delivery system may also be administered daily.

Suitable probiotic bacteria for use in this invention include any bacteria that are beneficial to the human microbiome. In accordance with the present invention, suitable probiotic bacteria include, but are not limited to, one or more purified forms of a bacterial family or genus selected from *Lactobacillus* crispatus, *Lactobacillus jensenii*, *Lactobacillus fermentum*, *Lactobacillus rhamnosus* (including *L. rhamnosus* GG, HA-111 and HA-114), *Bifidobacterium lactis*, *Lactobacillus plantarum* (including *L. plantarum* WCFS1), *Lactobacillus acidophilus* (including *L. acidophilus* GG and strains MUH-41, 0-61, L-1, 43121, DDS-1 and La-5), *Lactobacillus casei* (including *L. casei* GG), *Lactobacillus brevis*, *Bifidobacterium longum*, *Lactobacillus salivarius*, *Lactococcus lactis*, *Bifidobacterium bifidum*, *Bacillus coagulans*, *Lactobacillus bulgaricus*, *Lactobacillus gasseri*, *Lactobacillus reuterii*, *Lactobacillus Paracasei*, *Lactobacillus fermentum*, *Bacillus coagulans*, *Streptococcus thermophilus*, and the like, and mixtures thereof. In another embodiment, the probiotic bacteria include microbiome transplant samples collected from the human colon, rectum, vagina, skin, mouth, or throat.

The probiotic bacteria are contained within an inner chamber of the multi-chamber dosage form in an amount that is effective to promote a healthy microbiome of a subject. Multi-chamber dosage forms according to the present invention will contain between about one million to one trillion colony forming units (CFU) of probiotic bacteria. In one embodiment, multi-chamber dosage forms are provided containing between about one million to one trillion CFUs of probiotic bacteria and preferably between one hundred million and one hundred billion CFU's of the probiotic bacteria per dosage unit. In an another advantageous embodiment, the probiotic bacteria are freeze dried. The amount of freeze dried probiotic bacteria to be added to the inner chamber may be easily calculated knowing the CFU/mg of the freeze dried probiotic bacteria and adding the appropriate weighted amount to provide the one million to one trillion CFU per dosage unit. Since the freeze dried probiotic bacteria are dormant, there is no need for nutrients to sustain their viability until activation post release by the subject.

However, if active probiotic bacteria are used, it may be necessary to include suitable nutrients within the inner chamber to maintain the viability of the active probiotic bacteria until the dosage form is used. The amount of nutrient will of course depend on the desired shelf life of the dosage form. In certain circumstances, it may be advantageous for a subject to have a pharmacist or other health care professional prepare fresh multi-chamber dosage forms for a daily treatment regimen, or several dosage forms that would be shelf stable for use over a five to seven day treatment regimen.

In accordance with this embodiment of the invention, suitable nourishment sources for the probiotic bacteria include, but are not limited to, lactose, galactose, fructose, fructose oligosaccharides, isomaltose, inulin, dextrose, glucose, amylopectin, lactate, resistant starch, corn starch, oligosaccharides, combinations thereof, and the like. Multi-chamber dosage forms according to the present invention can contain between about 1 and about 20 wt./wt. % of one or more of the nourishment sources relative to the weight of the probiotic bacteria in the dosage unit. In an advantageous embodiment, multi-chamber dosage forms contain between about 5 and about 15 wt./wt. % of one or more of these nourishment sources.

The outer chamber of the multi-chamber dosage form of the present invention contains a matrix material that is solid at room temperature outside of the human body and in a dry environment, but which melts at body temperature and when in contact with mucosa of the rectum or vagina following insertion. For purposes of the present invention, "room temperature" is defined as an indoor temperature of about 70° F. One or more species of prebiotic nutrients may be dispersed within this matrix, optionally with pH stabilizing agents, or other acceptable beneficial agents. The prebiotic nutrients are selected from the group consisting of honey, plant-derived oils, animal-derived oils and fatty acids, fruit vinegars, acetic acid, butyric acid, butyrate, complex carbohydrates, fibers, apple cider vinegar, iron, calcium, potassium, vitamin B12, vitamin C and vitamin K, polyethylene glycol, hydrogels, cocoa butter, glycerinated gelatin, shea butter, petrolatum, mineral oil, shark liver oil, Vitamin A, Vitamin $B_6$, Vitamin D, Vitamin $K_2$ (MK 1), potassium, folic acid, L-carnitine, quercetin, magnesium, calcium, alpha-lipoic acid, fiber, omega-3 fatty acids, nuclear factor-like 2 activators, L-glutathione, L-glutamate and gamma-aminobutyric acid, lemon juice, lactic acid, chamomile, coenzyme Q-10, collagen, gelatin, green tea extract, lactose, galactose, fructose, fructose oligosaccharides, iso-maltose, dextrose, glucose, amylopectin, inulin, resistant starch, corn starch, oligosaccharides, rosemary leaf extract, oregano oil, curcumin, coffee, ginger, flax seed oil, green barley, agrimony, aniseed-basil, aniseed-fennel, cayenne, Echinacea, garlic, honey, molasses, horseradish, lavender, marshmallow, olive oil, milk, peppermint, slippery elm, buttermilk, goldenrod, St John's wort, uva ursi, yarrow, bee pollen, bee propolis, mint and the like, and mixtures thereof. In one advantageous embodiment, the source of nutrients is apple cider vinegar. The use of the matrix material in the outer chamber is designed so that all of the matrix material in the outer chamber melts and dissolves within the rectum or vagina to release the prebiotic nutrient material and the other beneficial ingredients to the area of delivery to be treated. Only after the prebiotic nutrients and other optional ingredients contained within the matrix material in the outer chamber are released does the formulation with probiotic bacteria in the inner chamber melt from the mucosal moisture and dissolve in the same area treated area.

In accordance with the present invention, the matrix material may be included in either the inner chamber of the multi-chamber dosage form, the outer chamber of the multi-chamber dosage form or in both chambers. In an advantageous embodiment, the matrix material is contained in both the outer chamber and the inner chamber of the multi-chamber dosage form. The outer chamber, according to the present invention, will contain between about 30 and about 100 wt. % matrix materials, preferably between about 40 and about 75 wt. % of the matrix material and advantageously contain between about 45 and about 60 wt. % of the matrix material. Essentially any pharmaceutically acceptable base material for the formulation of rectal or vaginal suppositories can optionally be used in combination with the fatty acid mixture to form the matrix material of the present invention. The matrix material comprises a mixture of fatty acids and includes one or more of the following; polyethylene glycol, hydrogels, cocoa butter, glycerinated gelatin, hard fats (such as hard fats from palm kernel oil, palm oil, soybean oil, cottonseed oil, crambe oil and the like), shea butter, coconut oil, semisynthetic derivatives, and mixtures thereof. According to one embodiment the mixture of fatty acids contains at least 90 wt. % saturated fatty acids. According to one embodiment at least 50 wt. % of the saturated fatty acids of the fatty acid mixture is lauric acid. In an advantageous embodiment, the mixture of fatty acids includes coconut oil. According to yet another advantageous embodiment, the mixture of fatty acids includes both coconut oil and shea butter. According to one embodiment, multi-chamber dosage forms according to the present invention further contains between about 0.5 and about 20 wt. % of vinegar, preferably apple cider vinegar. In one embodiment, multi-chamber dosage forms contain between about 5 and about 15 wt. % of apple cider vinegar. Apple cider vinegar is advantageously used because it comprises fermented juice from crushed apples. Like apple juice, it contains pectin; vitamins B1, B2, and B6, sodium, phosphorous, potassium, calcium, iron, magnesium, biotin, folic acid, niacin, pantothenic acid and vitamin C, which provide nourishment to the probiotic bacteria.

Considered a functional food, coconut oil has now been recognized by many in the healthcare community as a powerful intervention against immune system related diseases. Coconut oil is nutritious and contains lauric acid, which preliminary studies suggest is a disease fighting fatty acid. It is also rich in fiber, vitamins, and minerals. Coconut oil thus possesses abundant natural agents that may reduce fungus, pathogenic bacteria and the viruses that cause influenza, herpes, and other illnesses. The present invention incorporates the discovery that coconut oil has been found to be superior in enhancing prebiotic nutrient absorption. While not being bound by any particular theory, it is believed that because coconut oil is rich in triglycerides and medium chain fatty acids (MCFAs), which are smaller than long chain fatty acids (LCFAs), it permeates cell membranes easily, and does not require lipoproteins or special enzymes to be utilized effectively by a subject's body. When coconut oil is used in the compositions of the present invention it thereby serves a dual role of providing a support matrix for the probiotic bacteria and also as a means to promote absorption of the prebiotic nutrients as well as any beneficial compounds produced by the probiotic bacteria.

Depending on the particular area of a subject's body that is being treated, it may be advantageous to include one or more suitable pH stabilizing agents in the matrix material of the multi-chamber dosage form. For example, when the intended area of treatment is urogenital, then an optimum pH is acidic, i.e. in the range of from about 3.5 to about 4.5. If the pH of the vagina increases, i.e. it gets less acidic, the quality or amount of lactobacilli can fall and other non-healthy bacteria can multiply. This can result in infections such as bacterial vaginosis or yeast infections, which can cause symptoms including itching, irritation, odor, and abnormal discharge. Similarly, when the intended area of treatment is a subject's gastro-intestinal tract, then the pH is generally neutral, in the range of about 6.5 to about 7.5. Suitable pH stabilizing agents include citric acid, Vitamin C, sodium bicarbonate and the like and mixtures thereof.

Suitable lubricating agents may be used to coat an outer surface of the multi-chamber dosage form of the present invention. Suitable lubricating agents include polyethylene glycol, hydrogels, cocoa butter, glycerinated gelatin, shea butter, petrolatum, mineral oil, shark liver oil, and the like and mixtures thereof. The use of lubricating agents is particularly useful when the multi-chamber dosage form is in capsule form. Gelatin capsules are known to adhere to wet surfaces and the use of a lubricating agent can greatly improve the ease of use during insertion.

According to one aspect of the present invention, a multi-chamber dosage form is provided for the delivery of probiotic bacteria and prebiotic nutrients to the rectum or vagina to supplement and nourish the existing microbiome, wherein the composition includes the following ingredients:
  a) fatty acid matrix that melts at body temperature;
  b) one or more species of probiotic bacteria dispersed within the fatty acid matrix contained within an inner chamber;
  c) a source of prebiotic nutrients for the probiotic bacteria contained within an outer chamber; and
  wherein the matrix material comprises a mixture of fatty acids that are solid at room temperature and wherein the outer chamber completely surrounds the inner chamber.

According to one embodiment, the multi-chamber dosage form according to the present invention contains Vitamin C. Typical compositions contain between about 500 and 7500 IU of Vitamin C. In one embodiment, multi-chamber dosage forms are provided containing between about 1000 and about 5000 IU of Vitamin C. The multi-chamber dosage forms may optionally further include, in addition to Vitamin C; the vitamins provided by the apple cider vinegar, one or more anti-oxidant, anti-inflammatory or nutrient vitamins selected from Vitamin A (2000 IU-3000 IU), Vitamin B6 (2.0 mg-100 mg), Vitamin D (1000 IU-5000 IU), Vitamin K2 (MK7) (150 mcg), and combinations thereof. One or more anti-inflammatory nutritional supplements can also be added, examples of which include, but are not limited to, potassium, folic acid, L-carnitine, quercetin, magnesium, calcium, alpha-lipoic acid, fiber, omega-3 fatty acids, Nuclear factor-like-2 (NRF2) activators, L-glutathione, L-glutamate, gamma-aminobutyric acid (GABA), and the like.

Figure 4:
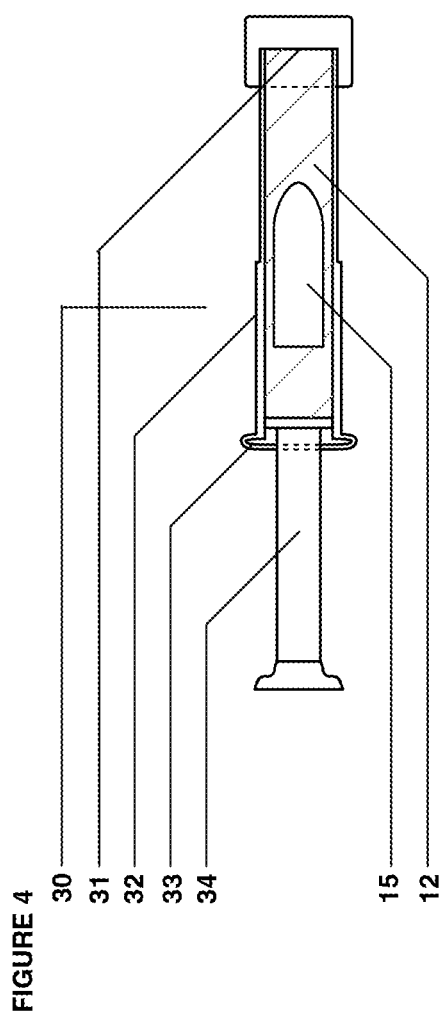
FIG. 4 depicts a cross-sectional top view of an applicator containing the dosage form of the present invention.
Figure 5:
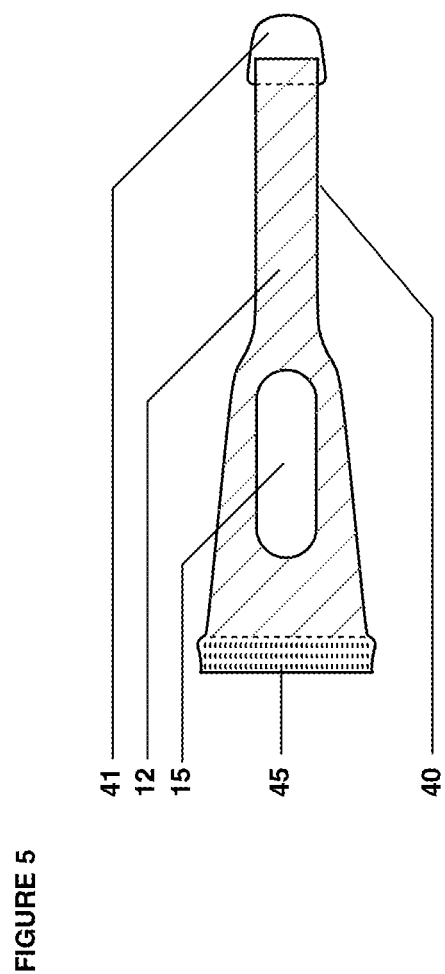
FIG. 5 depicts a cross-sectional view of an alternative applicator containing the dosage form of the present invention.

In an alternative embodiment the dosage form is a pre-filled applicator containing a multi-chamber dosage form having at least one inner chamber containing probiotic bacteria, the inner chamber being embedded in an outer chamber containing prebiotic nutrients in a blended fatty acid matrix. In accordance with this embodiment, the outer chamber and inner chamber are formed from appropriately sized capsules, such that the inner capsule is within and completely surrounded by the outer capsule. Referring to FIGS. 4 and 5, there are shown applicators adapted to deliver the multi-chamber dosage form of the present invention. FIG. 4 shows a plunger type applicator 30 having an elongate tubular barrel 32 adapted to contain the multi-chamber dosage form of the present invention. One end of the barrel 32 is open to permit the expulsion of the multi-chamber dosage form upon insertion of the plunger 34 and the opposite end is flared to permit easy grip by a subject when depressing the plunger 34. The open end of the barrel preferably is covered by a protective end cap 31. The barrel is pre-loaded with matrix material 12 and inner chamber 14 containing prebiotic bacteria.

FIGS. 5 and 6 show alternative designs for a prefilled applicator containing the multi-chamber dosage form of the present invention. In accordance with the embodiment shown in FIG. 5, the applicator is in the form of a sealed pouch. In this specific example the sealed pouch is a compressible tube 40. One end of the tube 40 has a crimp 45 to effectively seal that end of the tube 40 from leaking any of the contents. The opposite end of the tube 40 is open to allow the contents of the tube to be expelled upon compression of the tube 40 in use. The open end of the tube is conveniently covered by removable cap 41 to ensure that the inner contents of the tube 40 are not contaminated or otherwise exposed to external elements prior to removal of the cap 41 by the subject. The tube 40 contains the multi-chamber dosage form of the present invention including matrix material 12 in an outer chamber and probiotic bacteria in inner chamber 15. The inner chamber 15 is characterized in this embodiment as not being enclosed or contained within an inner capsule material. In accordance with this embodiment, the inner chamber is formed from a fatty acid matrix blended with probiotic bacteria. This inner chamber may be pre-formed and inserted into the outer chamber containing prebiotic nutrients in a separate blended fatty acid matrix, or may be injected to extruded into the outer chamber by conventional means. In an advantageous embodiment, the inner chamber 15 is formed from fatty acids that are slower dissolving upon exposure to a subject's internal body temperature than the fatty acids used to make up the outer chamber fatty acid matrix 12. For example, hard fats, shea butter and/or coco butter have higher melting temperatures than, for example, petrolatum or other low melting temperature fatty acids. The relative melting temperatures of the suitable fatty acids that make up the matrix material are well known to those skilled in the art and the choice of a particular fatty acid matrix is not critical, provided that the outer matrix material melts prior to the inner chamber.

FIG. 6 is similar to FIG. 5 except that the inner chamber 15 is defined by a capsule having an outer wall 14. In all other respects, the prefilled applicators in FIGS. 5 and 6 are the same. The melting point of the outer wall 14 is higher than the melting point of outer chamber fatty acid matrix 12, so that the prebiotic nutrients in the outer chamber will be released before the probiotic bacteria within the inner chamber 15.

When the multi-chamber dosage forms according to the present invention are intended for treating the urogenital region of a female subject, they may optionally contain from about 0.5 wt. % up to about 25 wt. % of one or more nutritional supplements. As used herein, the terminology "nutritional supplements" means any nutrients that are beneficial to administer to the vaginal area of a subject. These nutritional supplements include, but are not limited to vitamins, minerals, amino acids, fatty acids and the like. Suitable examples include from lemon juice, lactic acid, chamomile (fresh or oil), coenzyme Q-10, collagen, gelatin, green tea extract, rosemary leaf extract, oregano oil, curcumin, coffee, ginger, mineral oil, cocoa butter, shark liver oil, flax seed oil, green barley, agrimony, aniseed-basil, aniseed-fennel, cayenne, Echinacea, garlic, honey, molasses, horseradish, lavender, marshmallow, olive oil, whole leaf olive extract, milk, peppermint, slippery elm, buttermilk, goldenrod, St. John's wort, uva ursi, yarrow, bee pollen, bee propolis, and the like. Salicin from White Willow Bark (*Salix alba*) can also be used. Additional excipients, adjuvants, carriers, preservatives, and the like, may also be added, and are well known to persons skilled in the art.

Encapsulated formulations for delivery of precise quantities of live healthy bacteria measured to compliment, treat or assist with providing that which is missing in the intestinal mucosa of a diseased person with the ingredients described herein can be used to replace fecal transplants. In one embodiment, sub-compartmentalized capsules formulated to deliver probiotic bacteria from one sub-compartment and other ingredients described herein in at least one other sub-compartment are inserted high into the intestines through the anus by a method within the ability of a trained physician of ordinary skill specializing in this field.

Compositions according to the present invention can also include other beneficial microorganisms native to the human colon. Therefore, according to one embodiment of the present invention, compositions of the present invention include species of Archaea micro-organisms found in the human colon.

If the balance of bacteria is disturbed, this can lead to infection and inflammation. Bacteria called lactobacilli help maintain the vagina's pH balance at its normal low level (less than pH 4.5), which also prevents the growth of other organisms.

The present invention is useful to modify and improve the microbiome of the vagina of a female by inserting into the vagina the multi-chamber dosage form of the present invention that has been formulated to supplement this microbiome. The dosage form may be a capsule, suppository, prefilled applicator or pouch. Advantageous probiotic bacteria for use in treating the vagina include *Lactobacillus crispatus*, *Lactobacillus jensenii*, *Lactobacillus fermentum*, and the like and mixtures thereof.

There is an incredible amount of bacteria inside the human vagina, and they function to protect it. The good bacteria inside the human vagina:
  provide "numerical dominance"—they outnumber other potential harmful bacteria that might enter the vagina
  help keep the vagina's pH balance (how acidic the vagina is) at an even level, which helps keep the balance of bacteria healthy
  can produce bacteriocins (naturally occurring antibiotics) to reduce or kill other bacteria entering the vagina
  produce a substance that stops invading bacteria sticking to the vagina walls, which prevents bacteria invading the tissues.

Figure 7:
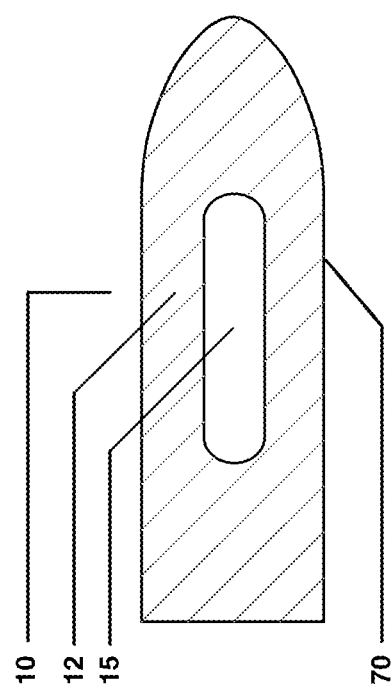
FIG. 7 depicts a cross-sectional view of a multi-chamber dosage form of the present invention wherein the dosage form is a suppository.
Figure 8:
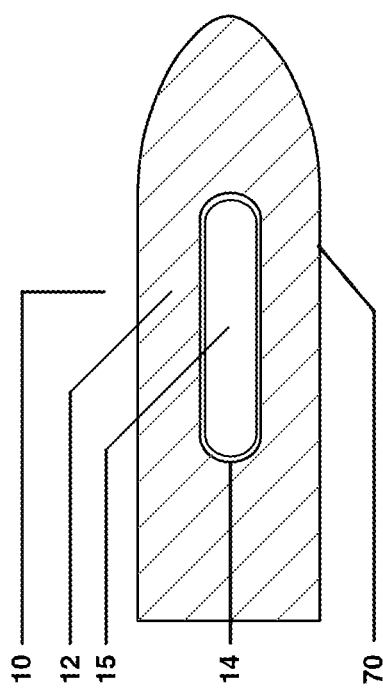
FIG. 8 depicts a cross-sectional view of a the multi-chamber dosage form of the present invention wherein the dosage form is a suppository wherein the inner chamber is a capsule surrounded by an outer fatty acid matrix.

The present invention provides a process for delivering healthy bacteria to the rectum or vagina by the use of an improved delivery system modeled after rectally and vaginally inserted products. The multi-chamber dosage forms may be used by digital insertion through the anus into the rectum, thereby bypassing the stomach and upper intestines. The multi-chamber dosage forms may alternatively be used by digital insertion into the vagina through the introitus therefore bypassing the stomach and upper intestines. The described multi-chamber dosage forms in this invention will be inserted by the subject in the same manner that over the counter rectal suppositories, or vaginal suppositories are used. As shown in FIGS. 7 and 8, the multi-chamber dosage form 10 is a suppository. As is well known in the art, suppositories differ from capsules in that they do not have an outer covering that is distinct from the materials that make up the suppository itself. Thus, in accordance with the present invention, the matrix material 12 is not enclosed in an outer wall, but instead the matrix material 12 itself, defines the outer boundaries of the suppository. FIG. 7 shows one embodiment wherein the suppository has an outer edge 70 defined by the matrix material 12. Enclosed within the matrix is an inner chamber 15. The inner chamber 15 is characterized in this embodiment as not being enclosed or contained within an inner capsule material. In accordance with this embodiment, the inner chamber is formed solely from freeze dried probiotic bacteria or may optionally be formed as a fatty acid matrix blended with probiotic bacteria. Thus, there is no requirement for an inner capsule to contain the prebiotic bacteria within the inner chamber 15. The inner chamber 15 may be pre-formed as a solid or semi-solid pellet and inserted into a pre-formed depression in the outer chamber containing prebiotic nutrients in a separate blended fatty acid matrix, or may be injected or extruded into the matrix material 12 forming the outer chamber by conventional means. In an advantageous embodiment, the inner chamber 15 is formed from fatty acids that are slower dissolving upon exposure to a subject's internal body temperature than the fatty acids used to make up the outer chamber fatty acid matrix 12. One method of slowing the dissolution rate of the inner chamber relative to the outer chamber is by choosing a fatty acid matrix wherein the melting point of the inner suppository 15 is higher than the melting point of fatty acid matrix material 12 in the outer chamber, so that the prebiotic nutrients in the outer chamber will be released before the probiotic bacteria within the inner chamber. For example, hard fats, shea butter and/or cocoa butter have higher melting temperatures than coconut oil or other low melting temperature fatty acids. For the outer chambers of the multi-chamber dosage forms illustrated in FIG. 7, examples of matrix materials for the outer chamber with a lower melting point (i.e. about 76°-90° F.) are coconut oil and semisynthetic fats customized for suppositories. Oils and fats may either be pure or blended to achieve a specific melting point, which is from about 5° F. to about 20° F. lower than the melting point of the matrix in the inner chamber. For the inner chamber, illustrated in FIG. 7, suitable fats include shea butter, cocoa butter, and semisynthetic fats with higher melting points (i.e. about 90° F. to about 98.5° F.) than the matrix of the outer chamber. These fats may be either pure or blended to achieve a specific melting point. Both chambers of these products would melt in the rectum or vagina at temperatures equal to or below internal body temperature (98.6° F.). The relative melting temperatures of the suitable fatty acids that make up the matrix material are well known to those skilled in the art and the choice of a particular fatty acid matrix, is not critical to the invention, provided that the outer matrix material melts prior to the inner chamber.

FIG. 8 is similar to FIG. 7 except that the inner chamber 15 is defined by a capsule having an outer wall 14. In all other respects, the suppositories shown in FIGS. 7 and 8 are the same.

When the multi-chamber dosage forms are in the form of a capsule or suppository, they may be packaged within conventional blister packs in a similar manner that rectal suppositories available over the counter for use in those with hemorrhoids are packaged. According to one embodiment the individual multi-chamber dosage forms within a blister pack are all the same. In another embodiment up to seven different formulations are provided within a blister pack to provide a patient with a full spectrum of probiotic bacteria and nutrients to be administered daily over the course of a week so the patient receives the variety of bacteria organisms present in a healthy gut microbiome during the treatment regimen.

Encapsulated formulations for delivery of precise quantities of live healthy bacteria measured to compliment, treat or assist with providing that which is missing in the intestinal mucosa of a diseased person with the ingredients described herein can be used to replace fecal transplants. In one embodiment, sub-compartmentalized capsules formulated to deliver probiotic bacteria from one sub-compartment and other ingredients described herein in at least one other sub-compartment are inserted high into the intestines through the anus by a method within the ability of a trained physician of ordinary skill specializing in this field.

There is a growing trend to swab babies-born by C section with the vaginal fluid from their mother. This is said to possibly give the baby a beneficial set of bacteria. In a vaginal birth, the baby ingests some of its first bacteria while in transit through the birth canal. Babies born by C section don't naturally get their mother's vaginal/anal bacteria and have to settle for the microbes living in the hospital environment or transferred via breast milk. Research suggests that it is a distinct disadvantage to C section babies as compared to babies born vaginally and makes these former babies more at risk for health issues that may include asthma, food allergies and hay fever and even obesity. Although there is some seeding of the fetal gut while in the uterus, the majority of the baby's bacterial seeding occurs during the vaginal birth process. At New York University Hospital, within 2 to 3 minutes of their birth, the mouth, body and anus of some C section babies are swabbed with gauze that had been placed in the mother's vagina for approximately an hour before the birth. In this way, the newborn is exposed to the microbiome of the mother as it would have been had it been born vaginally.

However, this approach assumes that the mother's vaginal/anal microbiome is healthy. To insure a healthy vaginal/anal microbiome in the mother-to-be, the present invention provides a method in which pregnant women can use these suppositories in the prenatal period. By introducing a favorable microbiome, this may translate to a healthier microbiome being delivered by swabbing after birth to the C-section newborn as well as to the newborn born vaginally through the birth canal and being exposed to the mother's vaginal/anal microbiome. The present invention is useful to modify the microbiome of the vagina of a female by inserting into the vagina the multi-chamber dosage form of the present invention that has been formulated to supplement this microbiome. Advantageous probiotic bacteria for use in treating the vagina include Lactobacillus crispatus, Lactobacillus jensenii, Lactobacillus fermentum, and the like and mixtures thereof.

The various embodiments herein may apply to each of the aspects of the invention. The embodiments are not intended to be interpreted as applying only to the aspect with reference to which they are specifically described.

Example 1

The following example is a rectal/vaginal multi-chamber dosage form product according to the present invention. The following ingredients were blended together in the order they are listed below. Each measured ingredient was added into an aseptic container and blended after each addition to create a smooth and homogenous paste mixture. The mixture was then placed into a conventional blister casing of the type used to produce rectal suppositories available for purchase over the counter for hemorrhoid management. These measurements were based on the relative amounts of prebiotic nutrients and probiotic bacteria necessary to maintain a healthy mucosa. The amounts may be increased or otherwise adjusted if the dosage form is being used for treatment or to replace FMT.

Coconut oil—2.5 ml-5 ml
Chamomile (fresh)—7 ml-1.25 cc
Sodium bicarbonate—0.75 ml-1.25 cc
Apple cider vinegar—0.7 ml-1.25 cc The inner chamber of the multi-chamber dosage forms were prepared by placing 100-350 mg of a blend of some or all of the following probiotic bacteria into a capsule:

L. acidophilus DDS 1
Bifidobacterium lactis
L. plantarum WCFS1
L. casei GG
L. rhamnosus GG
L. brevis
Bifidobacterium longum
L. salivarius
Strep. thermophilus
Bifidobacterium bifido The inner capsule is then pressed into blister casing containing the prebiotic nutrient paste and completely encased therein.

Example 2: Rectal Suppository

The following suppository ingredients were blended together in the order they are listed to form a uniform homogenous paste and compressed into a suppository mold around a capsule containing probiotics and sealed. These measurements are based on an amount necessary for healthy maintenance of the mucosa and dependent on the size of the suppository. Compositions may be adjusted using different or alternative bacteria specific for treatment or to replace FMT.

Coconut oil—2.5 ml-5 ml
Chamomile—0.7 ml-1.25 ml
Sodium bicarbonate—0.75 ml-1.25 ml
Apple cider vinegar—0.7 ml-1.25 ml
Inner capsule
Probiotic Blend selected from listed strains—105-1013 CFUs
L. acidophilus DDS 1
Bifidobacterium lactis
L. plantarum WCFS1
L. casei GG
L. rhamnosus GG
L. brevis
L. crispatus
L. reuterii
L. jensenii

*Bifidobacterium longum*
*L. salivarius*
Strep. *thermophilus*
*Bifidobacterium* bifido

Example 3

Vaginal Product: Multi-Chamber Capsule in Prefilled Applicator

This example describes a vaginal applicator product containing a multi-chamber dosage form prepared as described below and placed in the barrel of an applicator that had been prefilled with a prebiotic nutrient semisolid suspension containing a fatty matrix such as coconut oil, apple cider vinegar, lactic acid or lactate, vitamin C and decaffeinated green tea extract. The inner chamber of the multi-chamber dosage form contains one or more of the following strains:

*L. crispatus*
*L. iners*
*L. gasseri*
*L. jensenii*

To prepare multi-chamber dosage forms, capsule shell materials were selected from HPMC, pullulan, or gelatin (animal or plant-derived). Formulations were blended separately for the inner chamber and outer chamber. The inner chamber contained a mixture of probiotic bacteria with a fatty matrix. The outer chamber contained a prebiotic nutrient semisolid suspension containing a fatty matrix such as coconut oil, apple cider vinegar, vitamin C and decaffeinated green tea extract. The inner capsule was filled and sealed and placed in an outer capsule shell which was partially filled with the prebiotic nutrient formulation. The prebiotic nutrient blend in the inner capsule contained the following:

*L. acidophilus* DDS 1
*Bifidobacterium lactis*
*L. plantarum* WCFS1
*L. casei* GG
*L. rhamnosus* GG
*L. brevis*
*L. crispatus*
*L. reuterii*
*L. jensenii*
*Bifidobacterium longum*
*L. salivarius*
Strep. *thermophilus*
*Bifidobacterium* bifido After the inner capsule was encased in the outer capsule, it was suitable for use.

Example 4

Biofilm Disruption

Three healthy subjects, 2 females aged 50 and 60 and 1 male aged 70, used the suppositories for up to three years. The females were taking no prescription medications during this trial, while the male was taking antihypertensive drugs. The suppository composition as described in Example 2 was inserted daily into the subjects' rectum. Effects were closely observed and reported throughout the first month of use.

Within the first 3-7 days each of the participants' stool was observed and compared to the Bristol Stool scale for evaluation. The stools produced by the female subjects from day 1-3 were Type 2 and Type 5. Each had a strong odor and dark color and different types of stool formations occurred. The male subject reported stool type 7 for 24 hours between days 2 and 3. By day 5-7, all subjects experienced a discharge of a thin, slimy, long film similar in appearance to a pond scum like buildup was observed. This type of rectal discharge is not on the Bristol Stool Scale. This buildup was confirmed as being biofilm. Once this biofilm discharge began, it lasted 2-3 days and then it cleared up. Thereafter, all subjects reported normal healthy-looking stools. When compared to the Bristol Stool Scale Type, all stools were categorized as being 3 "Like a sausage but with cracks on its surface."

Throughout the next thirty (30) days, all subjects' stools were continually visibly healthy and compared to a healthy Bristol Stool Scale Type 3 and mostly Type 4. Odor, color and formation were viably healthy with no more evidence of the slimy film. Healthy noticeable changes in overall well-being began including mental clarity, vision, energy, weight loss, blood work. Because of the continual well-being the suppositories were used for approx. 3 years on and off until present. When any subject went off for a length of 6 months and began again the stool did produce a small amount of film again.

Interpretation of the Bristol Stool Scale

The seven types of stool are:
Type 1: Separate hard lumps, like nuts (hard to pass); also known as goat feces
Type 2: Sausage-shaped, but lumpy
Type 3: Like a sausage but with cracks on its surface
Type 4: Like a sausage or snake, smooth and soft
Type 5: Soft blobs with clear cut edges (easy to pass)
Type 6: Fluffy pieces with ragged edges, a mushy stool
Type 7: Watery, no solid pieces, entirely liquid
Types 1 and 2 indicate constipation, with 3 and 4 being the ideal stools as they are easy to defecate while not containing excess liquid, 5 tending towards diarrhea, and 6 and 7 indicate diarrhea.[10]

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein

What is claimed:

1. A method for enhancing the efficacy of probiotic *Lactobacillus* and/or *Bifidobacterium* bacteria directly delivered to the gastrointestinal system of a subject in need thereof, the method comprising the sequential steps of:
  administering to the gastrointestinal system of the subject one or more prebiotic nutrients in an amount effective to improve the receptivity of the gastrointestinal system for the probiotic;
  administering selected freeze-dried probiotic bacteria to the gastrointestinal system containing the prebiotic nutrient compound to the same area as the prebiotic;
  wherein the prebiotic nutrient and the freeze-dried probiotic bacteria are administered in a multi-chamber dosage form comprising:
  a) an inner chamber containing one or more species of freeze-dried probiotic selected from the group consisting of *Lactobacillus* and *Bifidobacterium* bacteria;
  b) a pharmaceutically acceptable matrix material that is solid at room temperature when in a dry environment, but that melts at body temperature when in contact with the mucosa of the rectum of the subject, wherein the matrix material fully encloses the inner chamber;

wherein the matrix material contains prebiotic nutrients for said probiotic bacteria and a mixture of fatty acids that are solid at room temperature but melt at a subject's body temperature, the prebiotic nutrients comprising one or more of vitamin C, apple cider vinegar and green tea extract, and wherein the dosage form is a capsule, a capsule embedded in suppository, a capsule embedded in prefilled applicator or a capsule embedded in prefilled sealed pouch.

2. The multi-chamber dosage form of claim 1, wherein said prebiotic nutrients comprise apple cider vinegar.

3. The multi-chamber dosage form of claim 1, wherein said mixture of fatty acids comprises at least 90 wt. % of saturated fatty acids.

4. The multi-chamber dosage form of claim 1, wherein at least 50 wt. % of the saturated fatty acids of said mixture of fatty acids is lauric acid.

5. The multi-chamber dosage form of claim 1, wherein said mixture of fatty acids comprises coconut oil.

6. The multi-chamber dosage form of claim 1, wherein said probiotic bacteria comprise one or more species of bacteria selected from the group consisting of *Lactobacillus rhamnosus, Bifidobacterium lactis, Lactobacillus plantarum, Lactobacillus acidophilus, Lactobacillus casei, Lactobacillus brevis, Bifidobacterium longum, Lactobacillus salivarius, Lactococcus lactis, Lactobacillus reuterii, Lactobacillus crispatus, Lactobacillus iners, Lactobacillus jensenii, Bacillus coagulans, Lactobacillus bulgaricus, Lactobacillus gasseri, Bifidobacterium bifidum* and mixtures thereof.

7. A method for improved delivery of probiotic bacteria to the gastrointestinal system of a subject in need thereof comprising administering to the subject a dosage form, comprising:
a) an inner chamber containing one or more species of freeze-dried probiotic bacteria selected from the group consisting of *Lactobacillus* and *Bifidobacterium* bacteria;
b) a pharmaceutically acceptable matrix material that is solid at room temperature when in a dry environment, but that melts at body temperature when in contact with the mucosa of the rectum of the subject, wherein the matrix material fully encloses the inner chamber;

wherein following administration, the dosage form first releases one or more prebiotics, the prebiotics comprising at least one selected from the group consisting of vitamin C, apple cider vinegar and green tea extract, to the gastrointestinal system of the subject in an amount effective to improve the receptivity of the gastrointestinal system to one or more species of probiotic bacteria and then releases one or more species of probiotic bacteria to the gastrointestinal system of the subject 0.5 to 60 minutes after the prebiotic nutrients in the outer chamber have contacted the treated area of the subject, thereby improving delivery of probiotic bacteria to the gastrointestinal system of a subject.

8. The method of claim 7, wherein the dosage form is a suppository, a capsule, a capsule with an enteric coat, a capsule embedded in suppository, a capsule embedded in prefilled applicator or a capsule embedded in prefilled sealed pouch.

* * * * *